United States Patent [19]
Bruchman et al.

[11] Patent Number: 5,879,383
[45] Date of Patent: Mar. 9, 1999

[54] BLOOD CONTACT SURFACES USING ENDOTHELIUM ON A SUBENDOTHELIAL MATRIX

[75] Inventors: William Carl Bruchman; Paul Christopher Begovac, both of Flagstaff, Ariz.

[73] Assignee: W. L. Gore & Associates, Inc., Newark, Del.

[21] Appl. No.: 885,512

[22] Filed: Jun. 30, 1997

Related U.S. Application Data

[63] Continuation of Ser. No. 424,849, Apr. 19, 1995, abandoned, which is a continuation-in-part of Ser. No. 235,757, Apr. 29, 1994, abandoned.

[51] Int. Cl.$^6$ .............................. A61F 2/06; A61F 2/02
[52] U.S. Cl. .................................. 623/1; 623/11; 623/66
[58] Field of Search .............................. 623/1, 11, 12, 623/66; 435/325, 366, 371; 514/12; 600/36; 604/6, 35, 48, 319

[56] References Cited

U.S. PATENT DOCUMENTS

| | | |
|---|---|---|
| 3,562,820 | 2/1971 | Braun . |
| 3,953,566 | 4/1976 | Gore ......................................... 264/505 |
| 3,966,401 | 6/1976 | Hancock et al. .......................... 8/94.11 |

(List continued on next page.)

FOREIGN PATENT DOCUMENTS

| | | |
|---|---|---|
| 531 547 | 3/1991 | European Pat. Off. . |

OTHER PUBLICATIONS

M. B. Herring et al. in "A single technique for seating vascular grafts with autogenous endothelium," *Surgery* 84:498–504 (1978).

J. Hoch et al. in "In vitro endothlialization of an aldehyde–stabilized native vessel," *J. Surg. Res.* 44:545–554 (1988).

P. A. Schneider et al., "Confluent durable endothelialization of endarterectomized baboon aorta by early attachment of cultured endothelial cells," *J. Vasc. Surg.* 11:365–372 (1990).

S.G. Lalka et al., "Acellular vascular matrix: A natural endothelial cell substrate," *Ann. Vasc. Surg.* 2:108–117 (1989).

L. Bengtsson et al., "Lining of viable and nonviable allogeneic and xenogeneic cardiovascular tissue with cultured human venous endothelium," *J. Thorac. Cardiovasc. Surg.* 106:434–443 (1993).

J. Hoch et al., "Endothelial cell interactions with native surfaces," *Ann. Vasc. Surg.* 2:153–159 (1989).

(List continued on next page.)

*Primary Examiner*—Shelley A. Dodson
*Attorney, Agent, or Firm*—David J Johns; Eric J Sheets

[57] ABSTRACT

This invention relates to improved blood contact devices such as vascular prostheses rendered antithrombotic through the use of recipient endothelial cells grown on an appropriate subendothelial matrix. The subendothelial matrix layer, which serves as the substratum for growing endothelial cells, may be obtained from either natural donor vessels or from in vitro tissue culture sources. This subendothelial matrix is used in situ on the donor vessel, or is grown or applied to a synthetic component, preferably porous expanded polytetrafluoroethylene. Once this subendothelial matrix is prepared, recipient endothelial cells are seeded onto this matrix substratum, which then serves as the immediate blood contact surface. The endothelial cells may be applied as an intra-operative procedure, or grown on the subendothelial matrix substratum in vitro until the cells establish a confluent monolayer. A key aspect of this invention is that living, recipient endothelial cells are grown on the appropriate subendothelial matrix substratum, thereby providing a substantially nonthrombotic blood contact surface. Furthermore, the likelihood of recipient immunological response is minimized. This invention results in vascular prostheses that are particularly useful for arterial bypass requiring a diameter of 6 mm or less.

41 Claims, 5 Drawing Sheets

U.S. PATENT DOCUMENTS

| | | |
|---|---|---|
| 3,988,782 | 11/1976 | Dardik et al. .............................. 623/11 |
| 4,050,893 | 9/1977 | Hancock et al. ......................... 8/94.11 |
| 4,098,571 | 7/1978 | Miyata et al. .......................... 422/100 |
| 4,187,390 | 2/1980 | Gore .................................... 174/102 R |
| 4,323,358 | 4/1982 | Lentz et al. ............................. 8/94.11 |
| 4,539,716 | 9/1985 | Bell ........................................... 623/1 |
| 4,546,500 | 10/1985 | Bell ........................................... 623/1 |
| 4,553,974 | 11/1985 | Dewanjee ................................ 8/94.11 |
| 4,804,382 | 2/1989 | Turina et al. ............................... 623/1 |
| 4,883,755 | 11/1989 | Carabasi et al. ..................... 435/240.2 |
| 4,960,423 | 10/1990 | Smith ......................................... 623/1 |
| 5,037,378 | 8/1991 | Muller et al. ............................. 600/36 |
| 5,429,938 | 7/1995 | Humes ................................. 435/240.2 |
| 5,549,674 | 8/1996 | Humes et al. ............................ 623/11 |

OTHER PUBLICATIONS

A. Schneider et al., "An improved method of endothelial seeding on small caliber prosthetic vascular grafts coated with natural extracellular matrix," *Clin. Mat.* 13:51–55 (1993).

Y. S. Lee et al., "Endothelial call seeding onto the extracellular matrix of fibroblasts for the development of a small diameter polyurethane vessel," *ASAIO Journal* 39:M740–M745 (1993).

Grimm et al., "Glutaraldehyde affects biocompatibility of bioprosthetic heart valves," *Surgery* 111:74–78 (1992).

H. Miwa et al., "Development of hierarchically structured hybrid vascular graft biomimicking natural arteries," *ASAIO Journal* 39:M273–77 (1993).

P. Zilla et al., "The endothelium: A key to the future," *J. Card. Surg.* 8:32–60 (1993).

P. Ortenwall et al., "Seeding of ePTFE carotid interposition in sheep and dogs: species dependent results," *Surgery* 103:199–205 (1988).

N. L. James et al., "In vivo patency of endothelial cell–lined expanded polytetrafluoroethylene prosthesis in an ovine model," *Artif. Org.* 16:346–53 (1992).

A. Albini et al., "Fibroblast chemotaxis," *Collagen Rel. Res.* 5:283–296, (1985).

W. Morzycki et al., "Tumor necrosis factor–alpha but not interleukin–1 induces polymorphonuclear leucocyte migration through fibroblast layers by a fibroblast–dependent mechanism," *Immunology,* 74:107–113, (1991).

BLOOD CONTACT SURFACES USING ENDOTHELIUM ON A SUBENDOTHELIAL MATRIX

This is a continuation application of Ser. No. 08/424,849, filed Apr. 19, 1995, abandoned, which is a continuation-in-part application of application Ser. No. 08/235,757, filed Apr. 29, 1994, abandoned.

BACKGROUND OF THE INVENTION

1. Field of the Invention

The present invention relates to improved blood contact surfaces for use in apparatus such as in artificial blood vessels and other implantable appliances and methods for producing the blood contact surfaces.

2. Description of Related Art

Synthetic materials are widely used to replace diseased or damaged portions of the human cardiovascular system. The use of grafts composed of synthetics such as polyethylene terephthalate and expanded polytetrafluoroethylene (ePTFE), has provided successful results in the replacement of large vessels such as the aorta, iliac, or femoral arteries. The application of these same synthetics, however, to small diameter arteries such as in coronary artery bypass or peripheral arterial bypass beyond the popliteal artery often produces thrombosis despite patency-enhancing pharmacological measures. Other applications of synthetics in which clot formation is a frequent problem include the replacement of veins, heart valves, and the artificial heart. Tissue-based prosthetics provide similar performance to synthetics, having acceptable function in some applications, but in others, still having the complication of thrombus formation. These thrombotic problems limit the usefulness of both tissue-based and synthetic devices, particularly in more demanding applications. Consequently, a goal of researchers for many years has been to develop a blood contact surface that provides for the reduction or elimination of thrombosis.

Natural blood contact surfaces, such as those found within blood vessels, possess mechanisms that prevent blood from clotting during normal passage along the surface. In the case of a mammalian artery, the immediate blood contact surface comprises a layer of non-thrombogenic endothelial cells (ECs). Immediately external to the endothelial cell layer is the remainder of the intima: a subendothelial matrix layer of basement membrane and underlying glycoprotein-bearing extracellular matrix, and the internal elastic lamina. Surrounding the intima layer is the multilaminate media structure containing smooth muscle cells (SMCs) and elastin, and surrounding this media is the adventitia, the most external layer comprised of fibroblasts and connective tissue. Both the subendothelial layer and media are generally considered to be thrombogenic in nature in order to maintain hemostasis when the vascular system is injured.

Intact endothelial linings are considered to be non-thrombogenic unless damaged. Because of their blood-contacting location, endothelial cells have been thoroughly investigated with respect to their anti-thrombogenic function. Endothelial cells are known to synthesize or bind a number of substances with coagulation-inhibiting or fibrinolytic function including heparan sulfate/antithrombin III, dermatan sulfate/heparin cofactor II, thrombomodulin/protein C/protein S, prostacyclin and tissue-type plasminogen activator. Furthermore, segments of endothelium-bearing autologous vessel transplanted from one site to another in an individual to bypass diseased vessels exhibit an incidence of thrombosis substantially less than that of synthetics used in the same application. For these reasons, it has been assumed that endothelial cells are responsible for the non-thrombogenic activity of vessels. According to this assumption, synthetic blood contact devices capable of thrombo-resistance similar to the native vasculature would require a blood contact surface of endothelial cells.

Numerous attempts have been made to provide prosthetic surfaces, and specifically vascular grafts, that include or develop an endothelial cell lining. The overwhelming majority of these attempts have been carried out as an intraoperative cell-seeding procedure. Intraoperative cell-seeding typically involves harvesting endothelial cells from the recipient during the procedure and immediately seeding these collected cells onto a vascular graft that has been pretreated with a substrate to enhance endothelial cell attachment. Substrates frequently applied to the synthetic surface include preclotted blood taken from the patient or extracellular matrix proteins such as fibronecfin, collagen, or laminin, either singly or in combination. This approach was first reported by M. B. Herring et al. in "A single staged technique for seeding vascular grafts with autogenous endothelium," Surgery 84:498–504 (1978). In this procedure, autologous cells were seeded onto a preclotted DACRON® graft. These seeded grafts demonstrated a decreased thrombus formation compared to control grafts without endothelial cells. In spite of the improved initial adherence of the cells to the synthetic surface afforded through the use of these various substrata, the shear forces resulting from blood flow nevertheless leads to the loss of a substantial fraction of the applied cells.

In a variation of the above, U.S. Pat. No. 4,960,423 to Smith describes the use of elastin-derived peptides to enhance endothelial cell attachment. Some studies have used combinations of extracellular matrix molecules and cells to provide a substrate for endothelial cell attachment and growth. For example, U.S. Pat. Nos. 4,539,716 and 4,546,500 to Bell describe means by which endothelial cells are grown on a living smooth muscle cell-collagen lattice. In addition, U.S. Pat. No. 4,883,755 to Carabasi et al. describes a technical method for seeding endothelial cells onto damaged blood vessel surfaces.

Alternative means of growing endothelial cells on vascular grafts have also been reported. For example, the use of physical force to apply endothelial cells to graft surfaces is described in U.S. Pat. No. 5,037,378 to Muller et al. In another example, U.S. Pat. No. 4,804,382 to Turina and Bittman describe the application of endothelial cells to a semi-permeable membrane in which the pores are filled with aqueous gels to allow endothelial cell coverage.

Another approach has been the seeding of endothelial cells onto biologically-derived surfaces, including pericardium, cardiac valve leaflets, amnion, and arteries. These efforts appear to have originated with J. Hoch et al. in "In vitro endothelialization of an aldehyde-stabilized native vessel," J. Surg. Res. 44:545–554 (1988), where the authors attempted to grow endothelium on ficin-digested, dialdehyde stabilized, bovine artery. Human venous endothelial cells were found to adhere to and spread on the remnant collagen surface of these enzyme-digested grafts, but no implant studies were performed. J. Hoch et al. also investigated the growth of endothelium on human amnion, on live, mechanically-scraped human artery, and again on ficin-digested, tanned bovine artery. (J. Hoch et al., "Endothelial cell interactions with native surfaces," Ann. Vasc. Surg. 2:153–159 (1989)) Although endothelial cell adhesion was observed on these surfaces by 2 hours, the longterm persistence of ECs on these surfaces was not examined, and, as in the previous study, none of these endothelialized materials were implanted as vascular substitutes. P. A. Schneider et al. showed that endothelial cells could be successfully seeded onto the remaining collagenous surface of baboon vessels from which the intima was removed. (P. A. Schneider et al., "Confluent durable endothelialization of endarterectomized baboon aorta by early attachment of cultured endothelial cells," *J. Vasc. Surg.* 11:365–372 (1990)) S. G. Lalka et al. used detergent extraction of canine arteries to produce an ethanol-fixed acellular vascular matrix onto which human umbilical vein endothelial cells were successfully seeded in vitro. (S. G. Lalka et al., "Acellular vascular matrix: A natural endothelial cell substrate," *Ann. Vasc. Surg.* 2:108–117 (1989))

In a study similar to that of Hoch et al. in *J. Surg. Res.*, supra, L. Bengtsson et al. successfully grew human venous endothelium on the luminal surface of devitalized vessel segments denuded of endothelium and subendothelium. (L. Bengtsson et al., "Lining of viable and nonviable allogeneic and xenogeneic cardiovascular tissue with cultured adult human venous endothelium," *J. Thorac. Cardiovasc. Surg.* 106:434–443 (1993))

It is emphasized that in none of the foregoing studies have attempts to provide endothelial linings to biological tissues been carried out on tissues with an intact subendothelium. Furthermore, in none of these attempts have the tissues been tested as chronic vascular substitutes following endothelialization.

Biological tissues destined for implant use are commonly subjected to a preservation treatment employing fixative agents such as glutaraldehyde, formaldehyde, dialdehyde starches, polyepoxy compounds, or alcohols. Glutaraldehyde is the most commonly used crosslinking agent because it provides reduced immunogenicity, excellent tissue preservation, and stability in the implant environment. The use of glutaraldehyde as an agent to produce articles derived from biological tissues suitable for implantation is specified in a number of U.S. Patents, including U.S. Pat. Nos. 3,562,820 to Braun, 3,966,401 to Hancock et al., 3,988,782 to Dardik, 4,050,893 to Hancock et al., 4,098,571 to Miyata et al., 4,323,358 to Lentz et al., and 4,378,224 to Nimni et al. Although glutaraldehyde-treated tissues have generally provided good implant outcome, it has been shown that unreacted, residual glutaraldehyde can result in the inhibition or death of cells grown in contact with the fixed tissue. Previous investigators (see, for example, L. Bengtsson et al. supra) have shown that growth of endothelium on fixed tissue can be inhibited by residual glutaraldehyde.

The problem of residual glutaraldehyde has been addressed by blocking the reactive site on the aldehyde groups. It is well known that residual or free aldehyde groups can be effectively blocked using compounds containing amino groups such as amino acids or proteins. Grimm et al. ("Glutaraldehyde affects biocompatibility of bioprosthetic heart valves," *Surgery* 111:74–78 (1992)) describe a postfixation treatment by which reactive aldehyde groups can be passivated. Endothelial cell-seeded, glutaraldehyde-fixed tissue showed uninhibited cell growth following a 48 hour exposure to 8% L-glutamic acid. Nashef et al., in U.S. Pat. No. 4,786,287, specify the use of solutions containing an excess of aldehyde-reactive amines to increase the rate of aldehyde diffusion from fixed tissue by maintaining a low concentration of free aldehyde. U.S. Pat. No. 4,553,974 to Dewanjee describes another method to prepare collagenous tissues for endothelialization using a surfactant-detergent treatment, followed by glutaraldehyde fixation and anti-calcification treatments. Although endothelium has been previously grown on tissue surfaces, the treatments employed, including ficin digestion, detergent treatment, and mechanical removal, each disrupt the subendothelial layer, resulting in increased thrombogenicity. Additionally, tissues such as pericardium or amnion do not, in the native state, possess the required subendothelial matrix.

Recent efforts to provide a substrate that supports endothelial cell linings on graft surfaces include the use of in vitro cultured extracellular matrix. A. Schneider et al. used corneal endothelial cells to produce extracellular matrix on ePTFE vascular grafts. (A. Schneider et al., "An improved method of endothelial seeding on small caliber prosthetic vascular grafts coated with natural extracellular matrix," *Clin. Mat.* 13:51–55 (1993)) After production of an extracellular matrix, these original cells were then removed using Triton X-100 and $NH_4OH$, and the tubes were seeded again with bovine aortic endothelium. This approach showed that endothelium could be successfully grown on the extracellular matrix lining the ePTFE grafts, however, no implant studies were performed. Another approach by Y. S. Lee et al. employed fetal human fibroblasts in culture to secrete extracellular matrix onto a polyurethane tube. The fibroblast cells were then removed by one of several methods and the remaining matrix seeded with human omental endothelial cells. This method resulted in a patent graft at 5 weeks after implantation into a rat aorta. (Y. S. Lee et al., "Endothelial cell seeding onto the extracellular matrix of fibroblasts for the development of a small diameter polyurethane vessel," *ASAIO Journal* 39:M740–M745 (1993))

A similar approach has also been taken by H. Miwa et al., "Development of a hierarchically structured hybrid vascular graft biomimicking natural arteries," *ASAIO Journal* 39:M273–77 (1993). In this case, smooth muscle cells are layered over a DACRON® graft in an applied artificial matrix of collagen type I and dermatan sulfate glycosaminoglycan. A layer of endothelial cells is then grown on the artificial matrix to serve as the blood contact surface.

Since the endothelium is the acknowledged source of the antithrombotic behavior of the normal vasculature, an endothelial lining has been widely regarded as the means by which improved antithrombogenicity of cardiovascular implants will be achieved. Actual testing however, has provided mixed outcomes. A number of studies have been conducted in animals, with some reporting clear improvements in patency as a consequence of endothelialization. Several studies, though, report equivocal outcomes with little measurable improvement. (P. Zilla et al., "The endothelium: A key to the future," *J. Card. Surg.* 8:32–60 (1993)) P. Ortenwall et al., for example, showed similar patency outcomes between seeded and control grafts in both sheep and dogs. (P. Ortenwall et al., "Seeding of ePTFE carotid interposition grafts in sheep and dogs: species dependent results," *Surgery* 103:199–205 (1988))

Although the collective results of experimental seeding studies conducted in animals are suggestive of a performance improvement due to the addition of recipient endothelial cells, the data do not indicate a performance improvement to the level expected with the use of the autologous vessel. For example, in a test conducted in sheep, N. L. James et al. report that only one of six (1/6) endothelial cell seeded grafts was patent in comparison to six of six (6/6) autologous artery grafts. (N. L. James et al., "In vivo patency of endothelial cell-lined expanded polytetrafluoroethylene prostheses in an ovine model," *Artif. Org.* 16:346–53 (1992)) Similarly, application of the above described endothelialization methods to synthetic vascular implants in humans has shown little demonstrable improvement in patency, despite the observation that grafts seeded with recipient cells become endothelialized, at least in some cases. (P. Zilla et al., "The endothelium: A key to the future," *J. Card. Surg.* 8:32–60 (1993)) Thus, the actual clinical outcome achieved with endothelial-lined synthetics has not met the expectations raised by animal studies.

SUMMARY OF THE INVENTION

The present invention is directed to an improved blood contact surface suitable for use in artificial blood vessels and other implantable blood contact appliances.

A key element of the present invention is the combination of living endothelial cells of vascular origin attached to an appropriate subendothelial matrix to form a composite. This composite provides an improved patency performance compared to currently existing vascular graft prosthetics, particularly in small diameter applications. Donor cardiovascular tissue, having had its vascular endothelial cells removed, can be used to provide an appropriate subendothelial matrix for use in the present invention. Alternatively, an appropriate subendothelial matrix layer can be obtained by removing the subendothelial matrix layer from a native vascular surface and transferring it to a synthetic component. In yet another method, an appropriate subendothelial matrix layer can be grown in vitro using endothelial cells in combination with smooth muscle cells. In any case, the original endothelium is removed, exposing the subendothelial matrix layer for subsequent seeding with recipient vascular endothelial cells. Autologous vascular endothelial cells are preferred for seeding a subendothelial matrix layer of the present invention. Genetically engineered endothelial cells hating immunogenic cell surface factors removed may also be suitable for use in the present invention. In an optional step, the subendothelial matrix layer may be preserved prior to seeding with vascular endothelial cells. The term "preserved subendothelial matrix layer," in the instant specification, refers to a subendothelial matrix layer, that has been treated with a fixative solution, such as glutaraldehyde, to chemically stabilize the matrix and thereby preserve the subendothelial matrix layer as a surface upon which vascular endothelial cells attach and grow to form a direct blood contact surface. Once an appropriate subendothelial matrix layer is isolated and optionally preserved, living vascular endothelial cells are seeded onto this matrix and allowed to grow to confluency to form a direct blood contact surface. A subendothelial matrix layer of the present invention, preserved or unpreserved, also serves as a direct blood contact surface in the absence of recipient vascular endothelial cells attached to and growing on the subendothelial matrix layer. Thus, the final blood contact surface comprises a subendothelial matrix substratum preferably with endothelial cells attached to the substratum. In the absence of complete recipient endothelial cell coverage, the subendothelial matrix itself also serves as a blood contact surface.

Accordingly, the present invention comprises a blood contact surface which comprises a substratum comprising a subendothelial matrix layer that supports attachment and growth of applied cardiovascular endothelial cells, a layer of applied cardiovascular endothelial cells attached to the subendothelial matrix layer, wherein the cardiovascular endothelial cells serve as a direct blood contact surface and wherein, in the absence of cells attached to the substratum, the substratum serves as a direct blood contact surface.

While the present invention is particularly applicable to blood vessels and similar appliances, it may be applied to many areas where substantially nonthrombotic blood contact surfaces must be provided. Examples of other appliances that may be produced in accordance with the present invention include, without limitation, flexible sheets, heart valves, artificial hearts, artificial organs such as implantable artificial kidneys, and others.

DESCRIPTION OF THE DRAWINGS

The operation of the present invention should become apparent from the following description when considered in conjunction with the accompanying drawings, in which.

DETAILED DESCRIPTION OF INVENTION

Figure 1:
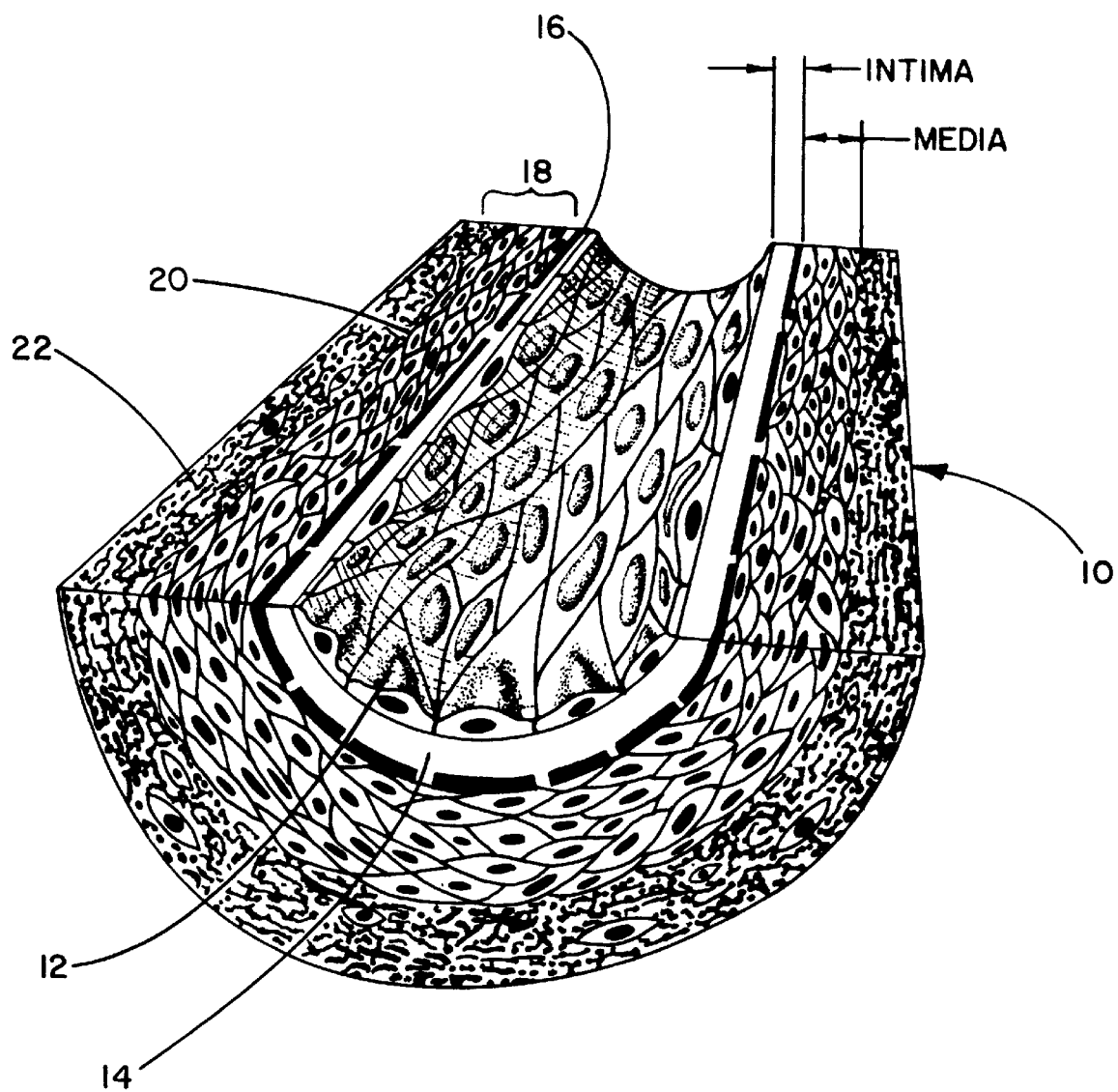
FIG. 1 is a perspective sectional view of a mammalian artery.

By way of introduction, FIG. 1 illustrates the structure of a typical mammalian artery (10). The artery (10) structure consists of an intima layer having an innermost layer of endothelial cells (12), a subendothelial matrix layer (14) consisting of basement membrane and other extracellular matrix components, and an internal elastic lamina layer (16). External to the intima is a media layer (18) composed of smooth muscle cells (SMC) (20), and finally a fibrous connective tissue or adventitia layer (22).

The present invention is directed to improved blood contact surfaces, such as those used in artificial blood vessels and other blood contact appliances. It is recognized that the endothelium provides the primary antithrombotic character to the surface of the native vasculature. Despite this, implant testing shows that endothelial-lined prostheses exhibit only equivocal improvements in patency in humans in comparison to the results achieved with the non-endothelialized prostheses alone. Since the endothelium is thought to be the sole source of antithrombotic properties, the absence of patency improvement in the human is startling.

It has been discovered that an additional element is necessary in order to realize the antithrombotic properties of the endothelium on prosthetic surfaces. It has been found that the antithrombotic function of an endothelialized surface is dependent upon the presence of an appropriate biological substrate, specifically a subendothelial extracellular matrix- layer. Although the subendothelial matrix is widely believed to be highly thrombogenic, in the absence of this layer, an endothelial lining confers only a marginal performance advantage to the blood contact surface.

In the present invention, three general methodologies have been developed to obtain an appropriate subendothelial matrix layer on which vascular endothelial cell growth can be achieved. The first method utilizes donor cardiovascular tissues from which the original endothelium has been removed, but the intact subendothelial matrix is preserved in situ. In the second method, the subendothelium from donor cardiovascular tissues can be removed, and applied to a synthetic component. In the third method, the desired subendothelial layer can be synthesized directly on an appropriate surface using in vitro cell culture techniques. With the third method, both smooth muscle cells and endothelial cells are required to produce the appropriate extracellular matrix by co-culture methods. Once a subendothelial matrix surface is prepared by one of these three means, recipient endothelial cells can either be grown to confluence prior to implantation or can be seeded onto the surface at the time of implant to form a direct blood contact surface, thereby providing an endothelialized graft with improved patency performance.

Irrespective of which of the above sources is employed, the subendothelial matrix of the present invention has several advantages over previously used surfaces. First, the endothelial cells that grow on a subendothelial matrix surface are tenaciously adhered, reducing concerns for cell loss. As a result, the endothelial cells tend to quickly reach and maintain confluence in comparison to other surfaces. Second, the combination of the subendothelial matrix and the endothelial cells is much less prone to thrombosis than an endothelial layer lacking the subendothelial matrix. Third, despite the findings of the bulk of the literature to the contrary, the subendothelial matrix itself has antithrombotic properties and can serve as a direct blood contact surface. This is of particular value when the present invention is practiced with intraoperative cell seeding. Under these conditions, the graft can be seeded with recipient endothelial cells with reduced concern for thrombus deposition that could compromise graft function before the cells grow to confluence. Moreover, that same thrombus could itself interfere with subsequent cell coverage of the surface.

Previous attempts to employ endothelial cells to provide antithrombotic surfaces have not recognized the necessity of the combination of endothelial cells and subendothelial matrix, as does the present invention. A key element of the present invention, therefore, is that the final endothelial cell layer be grown on the appropriate matrix. The appropriate matrix, as contemplated by the present invention, is either the native subendothelial matrix found in the cardiovascular system or the matrix produced by an appropriate co-culture of endothelial cells and smooth muscle cells. Since the subendothelial matrix layer is susceptible to damage by mechanical, enzymatic, or certain chemical processes, it should be prepared accordingly in order to preserve its nonthrombotic properties. One of the critical requirements of the present invention is that the subendothelial matrix be maintained in an intact form.

Preparation and Use of Native Subendothelial Matrix

The starting material for graft fabrication is donor cardiovascular tissue obtained from a vertebrate species, preferably a mammalian species including, but not limited to, bovine, porcine, ovine, equine or primate, including human sources. Avian sources may be useful as well. The cardiovascular tissue may be obtained from the heart, arterial vessels, venous vessels, and/or capillary beds. For example, arterial vessels may be obtained by freezing a limb intact or by immediate dissection of the appropriately sized vessels. If the limb segments are initially frozen, the limbs should be thawed first, then the vessels dissected free and placed into 4° C. saline buffer at physiological pH for further processing. Appropriate saline solutions include any number of physiological balanced salt solutions, including, but not limited to, Dulbecco's phosphate-buffered saline, Earle's balanced salt solution, Hanks' Balanced Salt Solution (HBSS), or phosphate buffered saline, for example. Processing entails dissection of the extraneous adventitial tissue and the ligation of any branch segments with polymeric suture material. Once these steps have been carried out, the vessel segments are ready for further processing to remove the endothelial cell layer.

The removal of the endothelial cell layer from the subendothelium must be carefully performed in order to maintain the intact subendothelial matrix and its nonthrombotic properties of the subendothelium. The use of overly aggressive techniques, such as detergent stripping, are found to damage the subendothelial matrix.

Figure 2:
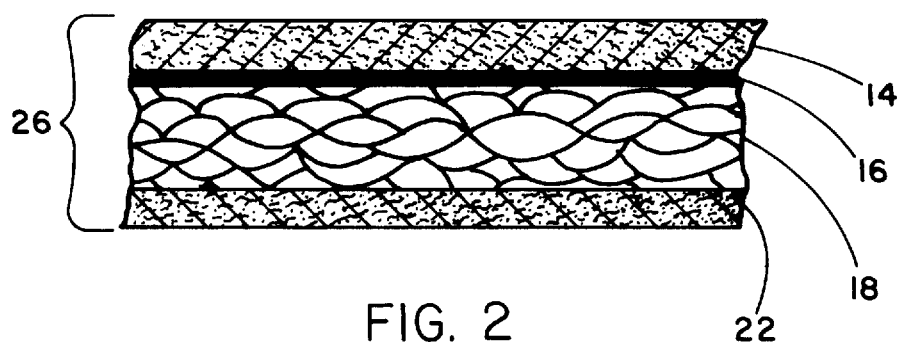
FIG. 2 is a sectional view through the longitudinal axis of a mammalian artery with the endothelial cell layer removed exposing the subendothelial layer (14).

There are a number of relatively simple agents and methods that will remove the endothelial cell layer without adversely affecting the subendothelial matrix. The subendothelium may be treated with a mild chemical stripping solution, such as, ammonium hydroxide ($NH_4OH$), for example. One such treatment may consist of incubating the vessel lumen in an aqueous $NH_4OH$ solution at a concentration of about 0.01M to about 0.5M, for a period of about 30 seconds to about 60 minutes followed by flushing the vessel lumen with a buffer solution. In the preferred embodiment, the treatment involves treating the vessel with a 0.25M $NH_4OH$ solution for about 3 to about 5 minutes. The resulting artery structure is shown in FIG. 2.

Another suitable technique for endothelial cell removal is the use of air drying of the luminal surface. One contemplated air drying treatment involves flushing the vessel lumen with buffer followed by air drying for about 5 to about 10 minutes at a flow rate of about 500 to about 2000 cc/min for a 4 mm internal diameter vessel. Preferably, the flow rate is about 1000 cc/min. Following air drying, the vessel lumen is flushed with buffer to remove the endothelial cells and rehydrate the subendothelial matrix prior to further processing.

In another embodiment of the present invention, the endothelial cells are removed by exposing the artery to a series of freeze-thaw cycles, preferably greater than two, followed by a flushing of the artery lumen with a suitable solution such as HBSS (1.3 mM $CaCl_2$, 5 mM KCl, 0.3 mM $KH_2PO_4$, 0.5 mM $MgCl_2$, 0.4 mM $MgSO_4$, 138 mM NaCl, 4 mM $NaHCO_3$, 0.3 mM $NaHPO_4$, 5.6 mM glucose).

Once the subendothelial matrix surface has been prepared by endothelial cell removal as described above, a processing step is employed to prevent or minimize calcification of the vessel tissue following implantation. This technique utilizes a solvent solution to extract predominantly lipid components. One effective treatment involves immersing the artery in a solution of chloroform and methanol ($CHCl_3/CH_3OH$) at a volume:volume ratio of about 2:1 for a period of about 15 to about 60 minutes, with a preferred treatment period of about 20 to about 40 minutes. The vessel is then removed and rehydrated through immersion in a saline solution. Once re-hydrated, the graft can then be preserved in a manner described below. The chloroform and methanol treatment does not damage the subendothelial matrix, but serves to limit calcification of the artery once implanted. It is understood that other anticalcification treatments may be employed as well.

Following rehydration, the vessel is treated with a fixative in order to preserve the subendothelial matrix, to reduce immunogenicity, and to sterilize the vessel segment. Suitable fixative agents include, but are not limited to, alcohols, glutaraldehyde, formaldehyde, dialdehyde starches, or polyepoxy compounds, for example. In a preferred form, the vessel is fixed under pressure. This is accomplished by placing the vessel within a tube that will provide an appropriate internal diameter, filling the vessel with the fixing solution and pressurizing to about 21 to about 35 kPa. Suitable tubes for providing an appropriate diameter include, but are not limited to, an ePTFE graft such as those available under the trademark GORE-TEX® Vascular Graft from W. L. Gore & Associates, Inc., Flagstaff, Ariz., for example. The duration of pressure fixation is dependent upon the fixation agent and the concentration employed. If, for example, glutaraldehyde is chosen as the fixative agent, suitable solutions would include about 0.1–2.5% concentration in an appropriate buffer. The duration of pressure fixation would then be about 1 hour to about 72 hours, depending upon the glutaraldehyde concentration chosen. Buffers suitable for this use include, but are not limited to, N-2-hydroxyethylpiperazine-N'-2-ethane sulfonic acid (HEPES), acetate, 2(N-morpholino) ethanesulfonic acid (MES), 3-[N-morpholino] propanesulfonic acid (MOPS), tris hydroxymethyl aminomethane, phosphate, and others, for example.

In the preferred embodiment, the vessel is pressure fixed in 100% ethanol for about 2–72 hours, after which it is rehydrated using a graded ethanol series of decreasing concentration. It may be possible to use other agents such as formaldehyde or glutaraldehyde to provide additional fixation or for use as sterilants. If these agents are employed, however, an additional process step is required to block any residual aldehydes so that subsequent cell growth on the surface is not inhibited. Amino group containing solutions suitable for the blocking step include, for example, 0.1M glycine, Medium 199, or Dulbecco's Modified Eagle's Medium. Following fixation, or fixation/blocking treatments, the vessels are rinsed and stored in a sterile 4° C. normal saline solution until implantation or further use.

In addition to the embodiment of the present invention described above, two other embodiments of this invention employ either native subendothelium derived from vessel and transferred to a synthetic surface, or an analogue of the subendothelium grown on the synthetic surface via in vitro cell culture. In an optional step, the subendothelial layer of either method can be treated with a fixation agent such as glutaraldehyde. In comparison to blood vessels fixed with aldehydes, the decreased mass and diffusional distances of these very thin layers provide a decreased likelihood of residual aldehydes. A blocking step such as that described above for the blood vessel is still recommended however, to ensure the lack of cell growth inhibition.

The subendothelial matrix layer preserved by the above processes contains numerous extracellular matrix components. Using immunocytochemical assays, it has been determined that this subendothelial matrix layer includes chondroitin sulfate proteoglycans, fibronectin, collagen Type I, collagen Type III, collagen Type IV, and elastin.

Figure 3:
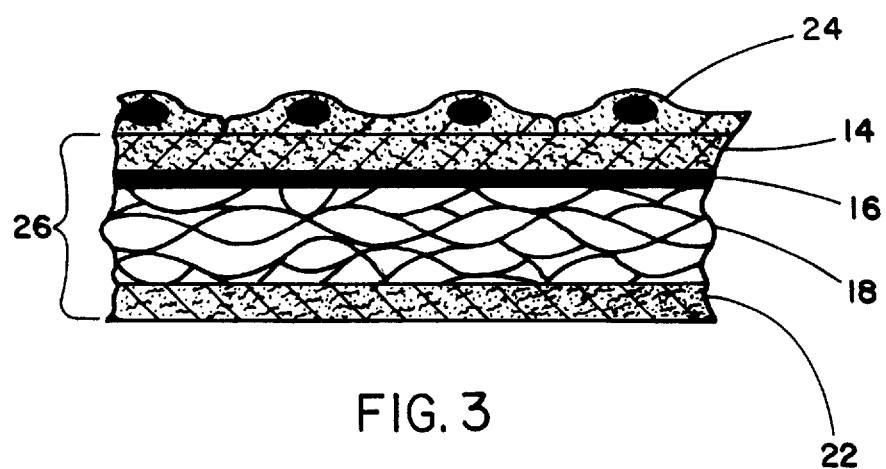
FIG. 3 is a sectional view of one embodiment of the present invention whereby living endothelial cells (24) have been applied to the surface of the mammalian artery structure (26) of FIG. 2.

Once the subendothelial matrix layer has been prepared, the matrix layer 14 serves as the substratum upon which recipient endothelial cells 24 are seeded and grown to produce a structure resembling that shown in FIG. 3. The endothelial cells may be applied in a number of ways. For example, endothelial cells may be harvested from the graft recipient as an intraoperative procedure and immediately applied to the subendothelial matrix substratum. Alternatively, endothelial cells may be isolated from a future recipient, grown in vitro on the subendothelial matrix substratum until confluent, then implanted into the patient.

In the two embodiments of the present invention that employ derived or in vitro subendothelial matrix layers, the nonthrombotic properties of the composite are supplied by the biological component, while the requisite mechanical properties are supplied by the synthetic component.

In one of these embodiments, the subendothelium is removed from the donor tissue and placed onto a synthetic component. In this case, the synthetic component supplies all of the required mechanical support. In another embodiment of the present invention, the synthetic component consists of an external sheath that is placed around the donor vascular tissue, and the support is thus a composite of that provided by the donor tissue and the external sheath. While the biological tissue is subject to degradative processes that could reduce its strength below that required for the application, the synthetic portion can resist these same processes where the appropriate polymer and fabrication are chosen.

One skilled in the art will recognize that minimum mechanical integrity requirements exist for each blood appliance application. One minimum requirement is that the appliance resist the forces imposed by blood pressure for the intended duration of a given application. The configuration must thus resist the hoop stress induced by blood pressure without rupture or aneurysm formation, and must similarly resist the stresses induced at the anastomosis without rupture, excessive suture hole elongation, or false aneurysm formation.

It is preferred to apply a sheath material to the external surface of the vessel to provide mechanical strength and to block cellular infiltration from the surrounding tissues. The pore size that is effective in blocking cell passage across the thickness of the sheath is dependent upon the thickness of the wall itself and the tortuosity of the pore connecting the outer surface with the inner surface of the sheath. In the case of regular uniform pores in a thin construction, ranging from about 10 µm to about 20 µm in thickness, the pores must be selected to be less than about 3 µm in diameter in order to block cell passage across the thickness of the sheath. This value is based upon Boyden chamber migration assays where the limit of fibroblast invasion through straight, uniform pores is about 5 µm to about 8 µm and the limit of invasion of leukocyte invasion through straight, uniform pores is about 3 µm to about 5 µm. (A. Albini et al., "Fibroblast chemotaxis," *Collagen Rel. Res.* 5:283–296, (1985); W. Morzycki et al., "Tumour necrosis factor-alpha but not interleukin-1 induces polymorphonuclear leucocyte migration through fibroblast layers by a fibroblast-dependent mechanism," *Immunology*, 74:107–113, (1991)) In the case of a thicker, more tortuous, or laminate structure, the individual pores can be somewhat larger and still serve as an effective barrier to the passage of cells across the layer.

For an ePTFE or similar fibrillated sheath, the pore size of the sheath is directly related to the fibril length of the sheath material. The fibril length should be chosen to form pores that resists cellular access through the sheath, while remaining permeable to macromolecules. In defining the ability of the sheath to resist cell ingrowth, a non-cellular assay method has been developed. Based upon the published values that 3 µm represents the lower limit of cell permeability through straight pores, 3 µm microspheres can be used to mechanically determine whether a given sheath will exclude particles of this diameter. Consequently, any sheath material that excludes 3 µm microspheres should effectively prevent cellular movement across the sheath.

In addition to the cell exclusion property, the sheath material is permeable to bulk flow of macromolecules. The term "macromolecules" is understood to include, but not be limited to, molecules having a molecular weight up to and including about 2,000,000 MW, for example. Suitable materials for the sheath include, but are not limited to, polytetrafluoroethylene (PTFE), polyethylene terephthalate, polypropylene, fluorinated ethylene propylene (FEP), and combinations of the above, among others, for example. In the preferred embodiment of the present invention, the sheath is microporous, constructed of ePTFE, permeable to bulk flow of macromolecules, impermeable to host cell ingrowth and of sufficient strength to serve mechanically as a blood vessel substitute even in the absence of the tissue it is intended to surround.

The sheath is installed by wrapping a mandrel with multiple layers of ePTFE film, such as those described in U.S. Pat. Nos. 3,953,566 and 4,187,390, each issued to Gore, both of which are incorporated herein by reference, and adhering the film to itself by heating the film and mandrel in an oven at about 380° C. for about 10 to about 20 minutes. The film tube is removed from the mandrel and the prepared tissue graft installed in the lumen of the polymeric tube. Other materials, or combinations of materials, may be similarly applied to the tissue tube using temperatures appropriate for the physical properties of the chosen material.

Figure 4:
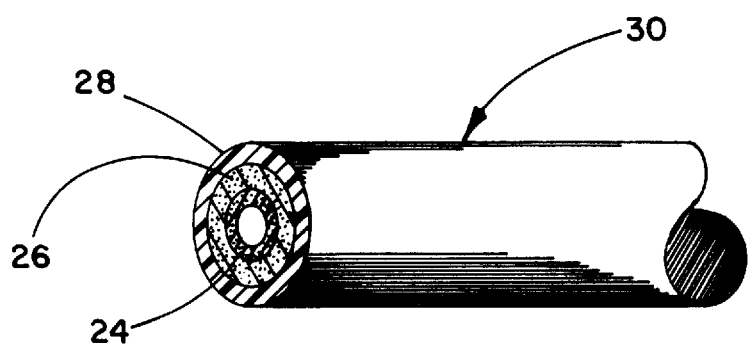
FIG. 4 is a view of a tubular vascular graft embodiment (30) of the present invention.

A composite structure is shown in FIG. 4 where the sheath (28) has been applied to the external surface of the artery wall (26) that has been covered with a layer of recipient endothelial cells (24) forming a tubular vascular graft (30).

Other methods of manufacturing the sheath material include placing the processed artery onto a mandrel and wrapping the graft with multiple layers of an ePTFE and FEP composite film, and heating the film layer very briefly from about 325° C. to about 350° C. to adhere the film wrap to itself on the vessel outer surface. The FEP-coated expanded PTFE film is made by a process that includes the steps of: a) contacting a porous PTFE substrate, usually in the form of a membrane or film, with another layer which is preferably a film of FEP or alternatively of another thermoplastic polymer; b) heating the composition obtained in step (a) to a temperature above the melting point of the thermoplastic polymer; c) stretching the heated composition of step (b) while maintaining the temperature above the melting point of the thermoplastic polymer; and d) cooling the product of step (c).

Another sheath construction method is the fabrication of a tubular form of ePTFE constructed according to U.S. Pat. No. 3,593,566 to Gore using a uniaxial expansion. The processed blood vessel is inserted into the ePTFE tube so constructed. As in the other forms of the sheath, the tubular form must be permeable to the passage of macromolecules but exclude the passage of cells.

Construction of the sheath is described in a U.S. patent application of Bruchman et al., entitled "Cell Excluding Sheath For Vascular Grafts," U.S. Ser. No. 08/235,071, filed Apr. 29, 1994, which is incorporated herein by reference.

The permeability characteristics of the sheath can be evaluated by testing with markers of known size, such as dextrans and polystyrene microspheres. For example, dextran, labelled with fluorescein (Sigma Chemical Co., St. Louis, Mo.), with an average molecular weight of about 2,000,000 MW can be used to test the ability of the sheath to pass macromolecules. Cell impermeability of the sheath can be tested using polystyrene microspheres (Polysciences, Inc., Warrington, Pa.), with a diameter of about 3 µm, at a concentration of about 2.5% solids in suspension, for example.

When testing the sheath for permeability with colored markers, the markers are suspended as an aqueous solution or suspension at concentrations sufficient to provide a distinctly visible color. Preferred concentrations of the compound of the marker solution is approximately 0.2 mg dextran/ml solution and approximately 0.02 ml microspheres/ml suspension, to yield about $4.5 \times 10^7$ beads/ml suspension. The evaluation of the sheath permeability occurs at about 23° C. The sheath is prepared for permeability testing by rendering it permeable to water, if necessary. For example, sheaths constructed of ePTFE are wetted with 100% ethanol and then flushed with water to remove the alcohol before testing.

To test the permeability of the sheath to macromolecules, the dextran test solution is instilled in the lumen of a sheath and pressurized to about 20.7 kPa using a syringe. The contents of the syringe are forced through the sheath and the liquid that filters through the sheath wall is collected and visually inspected against a white background for evidence of the colored dextran. In preparation for testing the permeability of a sheath for cells, the number of microspheres in the suspension are determined by using an appropriate counting device, such as a hemacytometer, for example. The permeability of the sheath is then tested by forcing the microsphere-containing suspension through the sheath material at about 20.7 kPa using a syringe. The syringe is refilled with water and the water also forced through the sheath at about 20.7 kPa. The liquid that filters through the sheath wall is collected and subjected to centrifugation at about 300×g for about 10 minutes. The supernatant is decanted and discarded and the pellet of microspheres is resuspended in a known volume of water. The number of microspheres in the resuspended pellet are counted and compared with the original suspension. The number of microspheres that pass through the sheath are expressed as a percentage of the number introduced into the lumen of the sheath.

An appropriate sheath for this application will pass the about 2,000,000 MW dextran at pressures at or below about 20.7 kPa so that the solution that filters through the sheath is visibly colored when viewed against a white background. Additionally, the sheath will not allow more than about 5% of the 3 µm microspheres to pass at a pressure of about 20.7 kPa.

Preparation and Use of Derived Natural Subendothelial Matrix

As previously described, a key element of the present invention is the use of the blood vessel subendothelial matrix layer as a substratum upon which endothelial cells are seeded or grown. The invention is practiced preferably by leaving the preserved subendothelial matrix layer in situ on the donor vessel, seeding the matrix surface with endothelial cells, and grafting the donor vessel intact. An alternative embodiment is the removal of the subendothelial matrix layer from the surface of the donor cardiovascular tissue and the re-application of this subendothelial matrix layer to a synthetic component, followed by the application of endothelial cells to the subendothelial matrix.

The first step in the process of applying a subendothelial matrix layer to a synthetic component is the removal of the endothelium from the donor tissue. The subendothelial matrix layer is then mechanically removed from the donor tissue using, for example, a scalpel blade. Only that layer of extracellular matrix superficial to the internal elastic lamina is removed. The intact internal elastic lamina is left attached to the donor tissue.

A number of methods of attachment of the subendothelial matrix layer to the synthetic component are possible. One preferred method of attachment of the subendothelial matrix layer to the synthetic component is to mechanically entrap the derived subendothelial layer onto the synthetic component. For example, the subendothelium derived from the luminal surface of bovine aortae is suspended in HBSS. An ePTFE vascular graft is wetted in 100% ethanol after mounting on syringe fittings and the solution containing the subendothelial matrix suspension forced through the interstices of the microporous graft using syringe pressure. As the solution is forced through the graft, the fragments of the subendothelial matrix are left behind entrapped in the interstices and on the surface of the graft. This applied subendothelial matrix serves as the substratum for the application of recipient endothelial cells.

Preparation and Use of In Vitro Subendothelial Matrix

Another important source of subendothelial matrix for use in the present invention is to create such a matrix in vitro. The source of subendothelial matrix for use in this embodiment of the present invention is based upon in vitro tissue culture methods. While the precise constituents producing nonthrombogenicity are not yet fully understood, the following technique may be suitable for producing the matrix.

Figure 5:
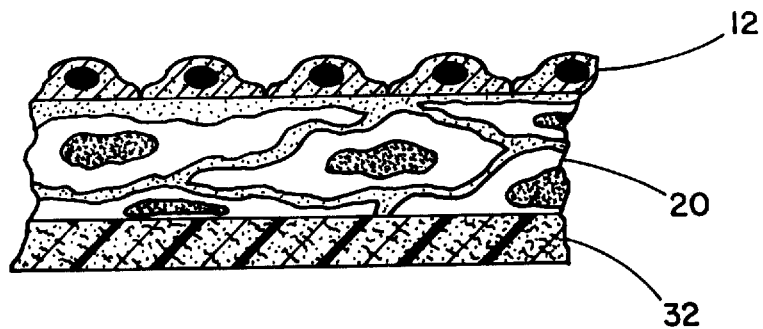
FIG. 5 is a cross-sectional view of a layer of endothelial cells (12) applied directly to a layer of smooth muscle cells (20) on a synthetic component (32).
Figure 6:
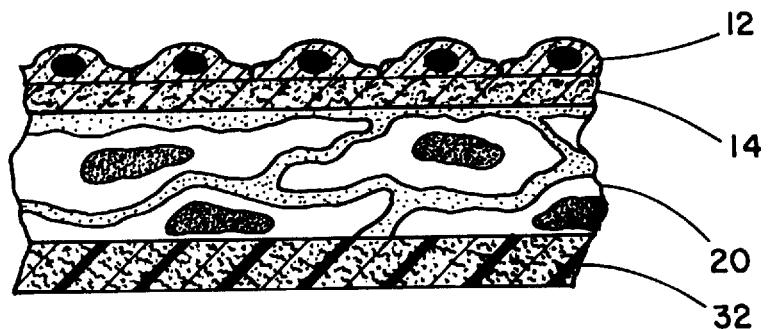
FIG. 6 is a cross-sectional view of the structure shown in FIG. 5 once a subendothelial matrix layer (14) has been generated between the endothelial cells (12) and the smooth muscle cells (20).
Figure 7:
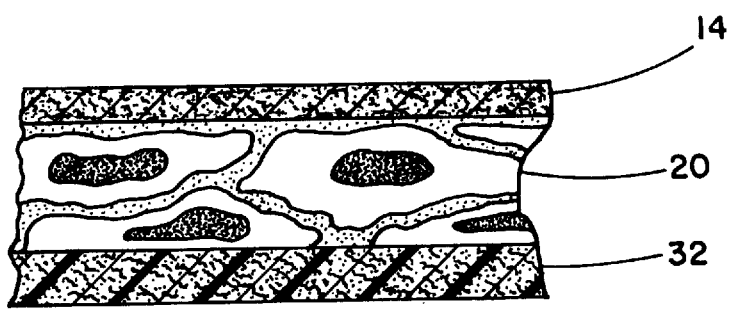
FIG. 7 is a cross-sectional view of the structure of FIG. 6 in which the endothelial cell layer (12) has been removed exposing the subendothelial matrix layer (14).

The present invention uses an analogue of the subendothelial matrix, synthesized with living vascular cells in vitro, to provide a substratum for seeding recipient ECs on synthetic materials. The steps of one embodiment of this process are illustrated in FIGS. 5 through 7. The generation of the in vitro subendothelial matrix appears to be the natural result of interaction between the endothelial cells and the smooth muscle cells. This subendothelial matrix is preferably produced by first culturing a biological substrate cell layer on a synthetic base material for a period of time. It is preferred that the substrate cell layer is composed of smooth muscle cells (SMCs), and most preferably vascular smooth muscle cells (VSMCs). Once the substrate cell layer is created, it is seeded with endothelial cells (ECs), preferably of vascular origin, to re-establish a conventional vascular cell relationship shown in FIG. 5. This structure consists of SMCs (20) grown on a synthetic base material (32) to which ECs (12) are seeded.

Following a culture period of sufficient time to allow both the SMCs and ECs to synthesize an in situ subendothelial matrix (14) as shown in FIG. 6, the ECs are specifically removed in such a manner as to leave the subendothelial matrix layer (14) intact overlying the SMCs (20) on a synthetic component consisting of a synthetic base material (32) as shown in FIG. 7. This composite graft may then be stabilized by glutaraldehyde fixation to minimize immunogenicity and preserve the subendothelial matrix layer.

The initial step in this process involves the preparation of a synthetic base material to support the SMC substrate layer and provide mechanical integrity. The preferred base material consists of a synthetic porous, expanded polytetrafluoroethylene (ePTFE) graft material, such as those commercially available from W. L. Gore & Associates, Inc., Flagstaff, Ariz., under the designation GORE-TEX® Vascular Graft. The 4 mm internal diameter vascular grafts used in the following description are commercially available product obtained from this source. The 2.5 mm internal diameter ePTFE tubing used in following description were constructed from CD 123 fine powder PTFE resin (ICI Americas) as taught in U.S. Pat. No. 3,953,566 to Gore, which is incorporated herein by reference. The tubes were expanded by stretching to produce a mean fibril length of about 28 $\mu$m. A fibril length of less than about 60 $\mu$m is preferred for this application. The finished tubes had an internal diameter of about 2.5 mm and a wall thickness of about 0.33 mm. Other suitable synthetic base materials may include, but not be limited to, the following: PTFE, polyethylene terephthalate, polypropylene, polyurethane, and polydimethyl siloxane, for example.

The fibril length of the porous expanded PTFE tubes produced as above is defined herein as the average of ten measurements between nodes connected by fibrils in the direction of expansion. Ten measurements are made in the following manner. First, a photomicrograph is made of a representative portion of the sample surface of adequate magnification to show at least five sequential fibrils within the length of the photograph. Two parallel lines are drawn across the length of the photomicrograph so as to divide the photograph into three equal areas with the lines being drawn in the direction of expansion and parallel to the direction of orientation of the fibrils. Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. The ten measurements obtained by this method are averaged to obtain the fibril length of the material.

The synthetic base material suitable for the present invention was further prepared in the following manner. Commercially available 4 mm diameter GORE-TEX® Vascular Grafts and ePTFE tubing measuring about 2.5 mm inside diameter were cut to about 7 cm lengths and syringe fittings were tied to both the proximal and distal ends of the grafts. Each graft was then mounted in a stainless steel wire holder and a plug inserted into the connector at the distal end of the graft. After steam sterilization, the grafts were prepared for cell-seeding by wetting the normally hydrophobic ePTFE with 100% ethanol. The ethanol in the graft interstices was displaced with about 80–100 ml of Hanks' Balanced Salt Solution (HBSS) (Gibco BRL, Grand Island, N.Y.) using a syringe attached to the proximal connector. Wetted grafts were stored in HBSS until used for cell-seeding.

Once the synthetic base material tube has been prepared, SMCs are applied to the luminal surface of this supporting structure. The preferred method is the use of positive pressure to force the media through the graft wall depositing SMCs onto the base material luminal surface. Other suitable means for applying the SMCs to the base material may include, but not be limited to: filling the base material tube lumen with a SMC suspension followed by a series of graft rotations to allow the SMCs to settle onto the surface uniformly; using negative pressure to draw the SMCs onto the base material; and using chemotactic agents, for example.

In one experiment, for example, the VSMCs were procured and applied to the synthetic base material in the following manner. Vascular SMCs were isolated by placing about 3–4 cm segments of carotid or femoral arteries obtained from greyhound dogs into a tube containing cold, sterile Medium 199 and 50 µg/ml gentamicin (Gibco BRL). In a laminar flow hood, the artery segment was slit longitudinally and the endothelial cells were removed by first rubbing the luminal surface with a sterile paper towel followed by scraping with a #10 scalpel blade. Thin strips of arterial media were peeled up with forceps and pooled into a puddle of HBSS in a sterile Petri dish. The strips were then placed into 25 cm² tissue culture flasks containing about 1.5 ml Smooth Muscle Cell Growth Medium (SMCGM) (43% Dulbecco's Modified Eagle Medium (DMEM); 43% Medium 199; 13% fetal bovine serum; 2 mM glutamine; 15 units/ml heparin; 23 µg/ml gentamicin; and 12.5 µg/ml endothelial cell growth supplement (Collaborative Biomedical Products, Bedford, Mass.)). Culture medium in the flasks was replaced when significant outgrowth of cells from the tissue pieces was observed. Twice weekly, the cells were then fed about 3–5 ml of the SMCGM, depending on the number of cells in the T-25 flask. The cells were generally passaged when about 60–90% confluent, and were usually split 1:4. Smooth muscle cell type was confirmed by morphological criteria, positive staining for alpha smooth muscle cell actin, and lack of uptake of acetylated low density lipoprotein which would indicate EC contamination.

For graft-seeding purposes, subconfluent VSMC cultures (passages 3–15, for example) were rinsed briefly with calcium-magnesium-free-HBSS (CMF-HBSS) and washed in CMF-HBSS for about 5 minutes. Cells were harvested using trypsin-ethylenediamine tetraacetic acid (EDTA) to release cells from the flask, followed by trypsin neutralization with SMCGM. Cells were pelleted at about 300×g for about 5 minutes and the pellet re-suspended in SMCGM for cell counting. After centrifugation, the cell pellet was re-suspended in SMCGM at a final concentration of about 2.5–6.0×10⁶ cells per 6–8 ml and transferred into a syringe in preparation for graft seeding. Grafts having an internal diameter of about 2.5 mm were seeded with about 2.5–3.5× 10⁶ cells/7 cm graft in about 6 ml SMCGM, for example, and 4.0 mm internal diameter grafts were seeded with about 4.0–6.0×10⁶ cells/7 cm graft in about 8 ml SMCGM, for example. Cell numbers were quantitated using a hemacytometer.

Graft seeding was performed by attaching the SMC-containing syringe to the proximal connector of the wetted graft and gently forcing the cell suspension into the graft and the media through the base material graft wall. The proximal fitting was then plugged and the seeded graft placed into a 16 mm culture tube filled with SMCGM with the graft wedged in the culture tube to prevent it from rolling in the tube. The culture tubes were capped securely and placed into an incubator at about 37° C. on a roller apparatus turning at about 10–50 rev/hr. The medium in the culture tubes was replaced at least twice weekly and grafts were cultured for a minimum of about ten (10) days before further processing or the addition of endothelial cells.

A layer of endothelial cells (12) attached to a substratum of smooth muscle cells (20) adhered to a synthetic base material (32) is shown in FIG. 5. This structure may be created in a variety of ways, with the preferred method being generating a single cell suspension of endothelial cells, filling graft lumen with the suspension, and allowing the endothelial cells to attach and spread on the SMC surface. Alternatively, small patches of endothelial cells may be directly harvested from a donor vessel and seeded into the graft lumen whereby they will attach and proliferate to cover the SMC substratum layer.

One method shown to be effective in isolating endothelial cells (ECs) was by using enzymatic methods to release ECs from arterial or venous vessels obtained from dogs. The vessel lumina were cannulated in a laminar flow hood, rinsed with HBSS, and filled with an endothelial cell harvesting enzyme solution in CMF-HBSS for about 15 minutes at about 37° C., for example. Suitable enzymes include, but are not limited to, collagenase, dispase, and trypsin. Endothelial cells were flushed into a sterile centrifuge tube and the ECs pelleted at about 300×g for about 5 minutes. The cells were then plated onto T-25 tissue culture flasks, grown at about 37° C. until nearly confluent and then passaged. Endothelial cell type was confirmed by morphological criteria, by positive staining for Factor VIII, and by uptake of acetylated low density lipoprotein.

For graft-seeding purposes, subconfluent endothelial cells (passages 2–10, for example) were rinsed briefly with CMF-HBSS and washed in CMF-HBSS for about 5 minutes. The cells were harvested by using trypsin-EDTA to release cells from the flasks followed by trypsin neutralization with complete Endothelial Cell Growth Medium (ECGM; 80% Medium 199, 16% fetal bovine serum, 2 mM glutamine, 15 units/ml heparin, 25 µg/ml gentamicin, 12.5 µg/ml Endothelial Cell Growth Supplement (Collaborative Biomedical Products, Bedford, Mass.)). The cells were pelleted at about 300×g for about 5 minutes, and the pellet re-suspended in ECGM at a final concentration of about 1.1–1.3×10⁶ cells/ml, for example. The cell suspension was transferred into a syringe for seeding.

A previously seeded SMC-graft, described above, was prepared for endothelial cell seeding by removing both end plugs and briefly rinsing the graft lumen with HBSS. The syringe containing the endothelial cell suspension was then attached to the proximal connector of the SMC-graft and the graft lumen filled with the cell suspension without forcing fluid through the graft wall. The syringe fittings were plugged and the grafts placed into 16 mm culture tubes filled with ECGM. Grafts were wedged into the tubes so they could not rotate independently of the culture tube during incubation.

Once the composite structure of endothelial cells (12) and smooth muscle cells (20) on a synthetic base material (32) was created, it resembled the structure shown in FIG. 5. The composite structure was placed under the following conditions that have proven successful. Culture tubes were incubated at about 37° C. in a roller apparatus turning at about 10–50 revolutions/hr. The medium in the culture tubes was replaced at least twice weekly with ECGM for the first week to establish ECs and then switched to SMCGM for the remainder of the culture period, a minimum of about 10 days total culture time.

Following culturing, a layer of subendothelial matrix (14) will form between the endothelial cells (12) and the smooth muscle cells (20) in the manner shown in FIG. 6. Generally the subendothelial matrix is less than about one µm in thickness.

Once a suitable layer of subendothelial matrix is created, the endothelial cell layer is removed through one of the following processes. Preferably, the endothelial cells are stripped by rinsing the graft about three times with HBSS, and treating with a 0.025M ammonium hydroxide solution for about 4–4.5 minutes to remove the endothelial cells, and rinsed again about three times in HBSS. Other suitable treatments may include 0.01–0.5M NH$_4$OH for about 30 seconds to about 60 minutes, for example. Other possibly effective methods of removing the endothelial cells may include air drying, or treatment with other stripping solutions, for example, chloroform, methanol, ammonium hydroxide, or sodium chloride, either alone or in combination. The chloroform/methanol treatment may also be employed to reduce potential calcification of glutaraldehyde fixed cellular material as well. Other treatments known to those skilled in the art may also be suitable. Once the endothelial cell layer is removed, the structure resembles that shown in FIG. 7.

Scanning electron microscopy inspection of representative samples treated in the above manner confirmed near total loss of the endothelial cells and the maintenance of the subendothelial matrix layer. It is understood that for purposes of the present invention, removal of endothelial cells from the subendothelial matrix layer in amounts greater than about 80% is considered to render the subendothelial matrix layer substantially free of donor endothelial cells.

The subendothelial matrix analogue exposed after removal of the endothelial cells contains numerous extracellular matrix components. Using immunocytochemical assays, it has been determined that the matrix includes chondroitin sulfate proteoglycans, collagen I, collagen III, collagen IV, elastin, and fibronectin all of which are present both on the exposed blood contact surface as well as within portions of the graft wall. In addition, laminin is an abundant component of the luminal subendothelial matrix blood contact surface and is present to a lesser degree within the graft wall.

Following EC removal, the grafts are optionally treated with a fixative. The purpose of this step is to preserve the subendothelial matrix layer, to reduce immunogenicity, and to sterilize the graft. This fixation can be accomplished by placing the graft into a fixing solution, such as, for example, 0.1–2.5% glutaraldehyde in a suitable buffer for about 1–72 hours depending upon the concentration of glutaraldehyde used. Suitable buffers may include, but are not limited to, N-2-hydroxyethylpiperazine-N'-2-ethane sulfonic acid (HEPES), acetate, 2-(N-morpholino) ethanesulfonic acid (MES), 3-[N-morpholino] propanesulfonic acid (MOPS), tris hydroxymethyl aminomethane, phosphate, and others.

In the preferred embodiment, the graft is fixed in greater than about 0.5% glutaraldehyde in 20 mM HEPES buffer for a minimum of about two hours. The fixed grafts are rinsed at least three times in sterile normal saline and washed for a minimum of about 24 hours in fresh sterile normal saline and then stored at about 4° C. in fresh sterile normal saline. Other suitable fixatives, such as formaldehyde, for example, may be used in addition to glutaraldehyde to assure sterility.

Figure 8:
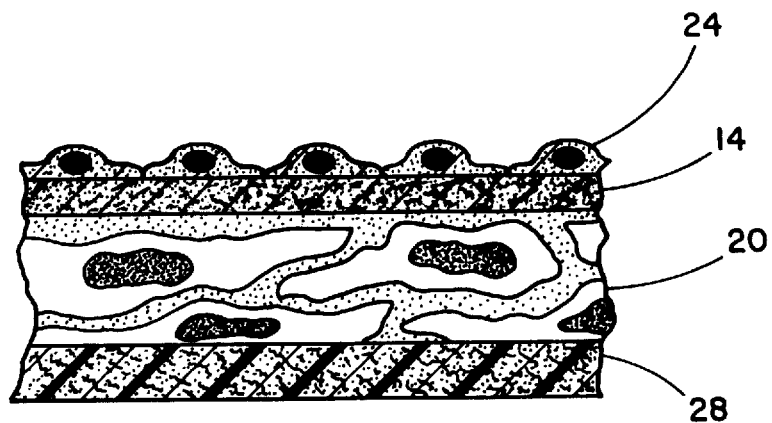
FIG. 8 is a cross-sectional view of one embodiment of the present invention wherein recipient endothelial cells (24) have been applied to the subendothelial matrix layer (14) shown in the structure of FIG. 7.

At this stage, remaining aldehyde reactive sites are blocked with an amino group containing solution. Suitable reagents for this procedure include, but are not limited to, 0.1M glycine, Medium 199, Dulbecco's Modified Eagle Medium, and other physiological culture media, for example. The graft is incubated in one of these solutions for a minimum of about 12 hours at about 37° C. Once the blocking step has been completed, the graft is placed into ECGM and incubated for several hours to equilibrate the vessel segment to the endothelial cell culture medium. Single cell suspensions of endothelial cells are then placed into the vessel lumen, both ends of the vessel plugged, and the graft placed into rotation culture to allow the endothelial cells to form a confluent monolayer on the surface as shown in FIG. 8. A structure resembling that shown in FIG. 8 is created with recipient endothelial cells (24) resting on an in vitro subendothelial matrix (14). The endothelial cells may be arterial or venous in origin and it is preferred that these cells be derived from the recipient to prevent immune responses.

It is also possible to produce the subendothelial matrix layer through a variety of other methods. One suitable method, for example, involves using mixed culture seeding in which both ECs and SMCs are combined in ratios of about 1:10 to 1:1 (EC:SMC) and both cell types are seeded onto the synthetic base material simultaneously. Once placed into culture, the ECs will form a confluent monolayer on the luminal surface thereby re-establishing the normal EC and SMC relationships. After extended co-culture, the subendothelial matrix will be produced between the cell layers. The subendothelial matrix layer may then be exposed as outlined above and processed accordingly.

While VSMCs are the preferred use as the substrate cell layer in the production of the subendothelial matrix layer of the present invention, it is recognized that it may be possible to use other cell types to provide a similar function. Among the other potential cell types are smooth muscle cells from the digestive system or urinary tract, as well as fibroblasts, among others, for example.

Additionally, while vascular endothelial cells are the preferred embodiment, it may also be possible to use other cell types to produce the subendothelial matrix layer in conjunction with the VSMCs, SMCs, fibroblasts, or other similar cell types. These cell types may include, but are not limited to, microvascular endothelial cells, corneal endothelium, glomerular epithelium, and mesothelial cells among others, for example.

Figure 9:
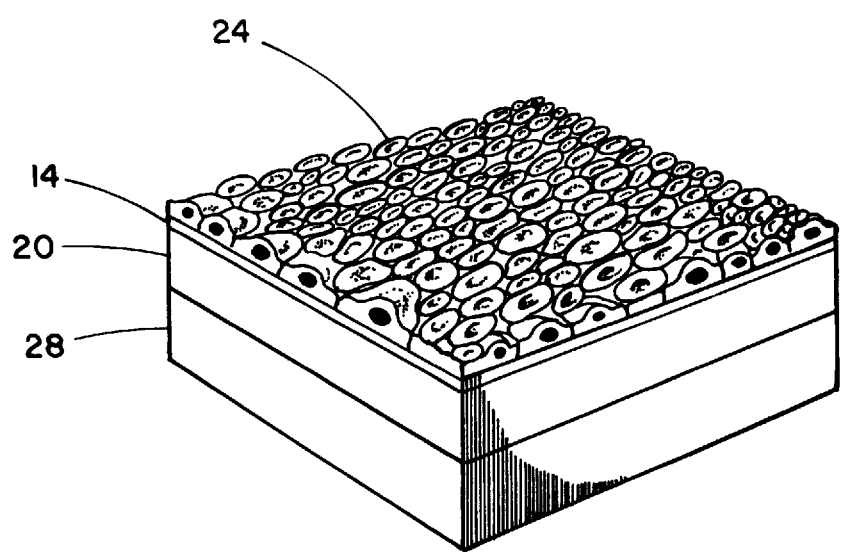
FIG. 9 is a view of one embodiment of the present invention wherein the structure shown in FIG. 8 is grown on a flat sheet of synthetic base material (28).
Figure 10:
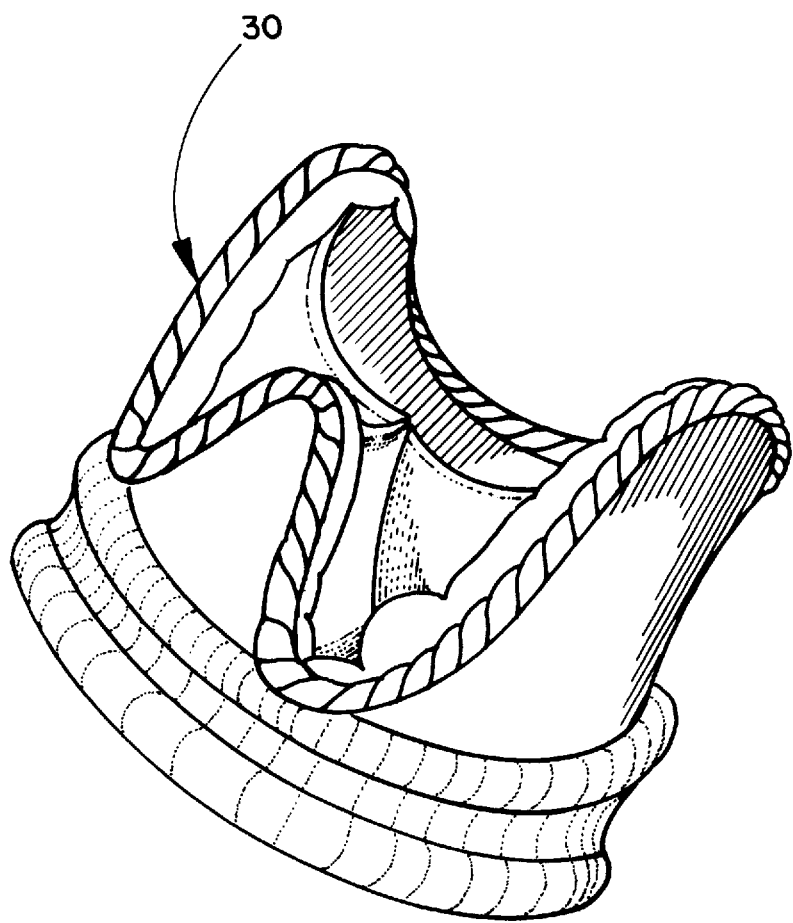
FIG. 10 is a view of a heart valve appliance (30) wherein the structure of FIG. 8 is employed.

While the present invention is particularly applicable to blood vessels and similar appliances, it may be applied to many areas where substantially nonthrombotic blood contact surfaces must be provided. Examples of other appliances which may be produced in accordance with the present invention include, without limitation, flexible sheets as shown in FIG. 9, heart valves as shown in FIG. 10, artificial hearts, artificial organs such as implantable artificial kidneys, and others.

Without intending to limit the scope of the present invention, the following examples illustrate how the present invention can be made and used.

EXAMPLES

Example 1

(Preserved Subendothelium Seeded with Endothelial Cells)

Pairs of canine carotid arteries were collected into a solution of HBSS containing 15% DMSO and flash frozen in liquid nitrogen. The artery segments were thawed, the lumen flushed with HBSS or normal saline, and the adventitia was removed by dissection. Both arteries were then everted and placed onto a 2.5 mm mandrel. The inventive artery, having an intact subendothelium without endothelial cells, was then removed from the mandrel and returned to its natural position. The control artery had the subendothelium removed by rubbing the endothelial surface of the artery with a cotton swab. The artery was then rinsed in HBSS and returned to its natural position for further processing. Both inventive and control arteries were subjected to further processing in parallel.

The arteries were each sleeved with a GORE-TEX® Vascular Graft of a diameter sufficient to produce a fixed graft of about 2.5 mm in diameter (usually 3.0 mm). The sleeved arteries were blotted dry and immersed in 100% medical grade ethanol. The arteries were pressure fixed in 100% ethanol for 2 hours at 23° C. under about 27.6 kPa pressure. After fixation, the artery segments were sterilized by overnight incubation in 70% ethanol. Following sterilization, the artery segments were rehydrated in a graded ethanol series into HBSS. The artery segments were then placed into Medium 199 for about 4–5 hours at 37° C., followed by an overnight incubation in fresh Medium 199. The segments were finally incubated 4–5 hours in ECGM at 37° C. Autologous venous endothelial cells were harvested by trypsinization and resuspended in ECGM at $1.1 \times 10^6$ cells/ml. The inventive and control arteries were filled with the cell suspension, the ends of each artery were plugged, and the arteries were incubated in culture tubes containing ECGM at 37° C. The day following seeding, the artery end plugs were removed and grafts cultured until the endothelial cells reached confluency on the artery luminal surface (generally greater than 7–10 days). The establishment of an endothelial cell monolayer was confirmed by staining with acetylated low density lipoprotein and scanning electron microscopy.

One day prior to implantation, the grafts were placed into Endothelial Serum Free Medium (Gibco BRL, Grand Island, N.Y.). Thirty minutes prior to implantation, the grafts were rinsed thoroughly in sterile 37° C. HBSS and stored in warm HBSS until implanted. These endothelialized inventive and control grafts were implanted as test pairs into the brachial arteries of an adult greyhound dog. Each graft of this pair was implanted into one brachial artery so that a direct comparison of the grafts within the dog was achieved. The vessel grafts, 2.5 cm long with an internal diameter of 2.5 mm, were a good diameter match to the native brachial artery of the adult greyhound recipient. Standard end-to-end surgical technique was used for implantation and no anticoagulants or antiplatelet agents were administered to the dogs at any time. The course of the implants was followed using duplex ultrasound examination. At 20 days postoperatively, the brachial implants were surgically exposed and the patency tested by transecting the artery distal to the implant location. The inventive graft having autologous endothelial cells grown on a preserved subendothelial matrix was widely patent and the control graft having autologous endothelial cells grown on a vessel without a preserved subendothelium was occluded. Thus, the use of a preserved subendothelium as a substratum for endothelial cells provided improved patency.

Example 2

(In Vitro Subendothelial Matrix Seeded with Endothelial Cells)

A vascular smooth muscle cell-endothelial cell matrix inventive graft fabricated as described in the detailed description above was prepared resulting in a base graft having a fixed, cell-generated subendothelial matrix. The inventive graft was placed into Medium 199 for a minimum of 12 hours at 37° C. to block unreacted aldehyde groups followed by incubation in Endothelial Cell Growth Medium (ECGM). Autologous venous endothelial cells were then seeded onto the graft subendothelial matrix surface by filling the graft lumen with a suspension of endothelial cells at a concentration of $1.1$–$1.3 \times 10^6$ cells/ml of ECGM. The graft was then wedged into a culture tube and placed into a 37° C. incubator on a roller apparatus for at least 10 days to allow the endothelial cells to establish a monolayer and become firmly attached. Endothelial cell coverage was confirmed by observing uptake of acetylated low density lipoprotein and scanning electron microscopy.

These endothelialized matrix inventive grafts were implanted as test pairs using control 30 μm ePTFE grafts into the brachial arteries of 2 adult greyhounds. Each pair was implanted into the brachial arteries of one dog so that a direct comparison of the vessels within each dog was achieved. The vessel grafts, 2.5 cm long with an internal diameter of 2.5 mm, were a good diameter match to the native brachial artery of the adult greyhound recipients. Standard end-to-end surgical technique was used for implantation and no anticoagulants or antiplatelet agents were administered to the dogs at any time. The course of the implants was followed using contrast angiography and duplex ultrasound examination. In both dogs, the inventive and control grafts were both patent at 74 and 27 days, respectively.

Example 3

(Mixed SMC-EC In Vitro Subendothelial Matrix Seeded with ECs)

Individual cultures of vascular SMC and EC were harvested for graft fabrication by removing growth medium, rinsing the cells with CMF-HBSS, followed by washing the cells in CMF-HBSS for 3–5 minutes. The CMF-HBSS was then removed and depending on flask size, 1.5–3.0 ml of trypsin-EDTA was added to release cells from the flask. Complete SMCGM was added to flasks to inactivate the trypsin, the cells were triturated, and pelleted by centrifugation at 300×g for 5 minutes. The supernatant was discarded, the cells were resuspended in SMCGM and cell counts were carried out, followed by a second pelleting of cells. The final individual SMC and EC cell pellets were resuspended in SMCGM at a concentration of $1 \times 10^6$ cells/ml, and then cell types mixed in EC:SMC ratios of 1:9, 1:4, and 1:2.

Several porous ePTFE tubes of 2.5 mm internal diameter, having about 30 μm fibril lengths, were cut to 7 cm and mounted onto syringe connector fittings. A polypropylene plug was fitted onto the distal end of each tube. The ePTFE tubes were wetted with 100% ethanol and the alcohol subsequently displaced with HBSS by pressurizing the tubes, thereby forcing HBSS through the porous tube walls. The wetted tubes were then stored in HBSS until seeding with the vascular cells.

Cell seeding of each ePTFE tube was carried out by placing $2.5$–$3.5 \times 10^6$ cells of the mixed SMC-EC suspensions into a total volume of 6–8 ml SMCGM in a syringe. The 2.5 mm internal diameter graft was seeded with 2.5 to $3.5 \times 10^6$ cells/graft. For each graft, a syringe containing the cell suspension was attached to the proximal syringe connector and the slurry was gently injected into the graft lumen. After placing cells into each graft, a second polypropylene plug was attached to the open connector to seal the cells in the graft lumen.

Each seeded graft was wedged into a 16 mm culture tube filled with SMCGM to ensure complete rotation of the graft during incubation. The culture tubes were capped securely and placed in a roller apparatus turning at about 10 rev/hr. in a 37° C. incubator. Seeded grafts were cultured for 7–10 days with fresh medium feedings every 2–4 days. During this culture period, the endothelial cells were segregated from the SMCs forming a confluent EC monolayer on top of the SMCs. This was verified by both scanning electron microscopy analysis and by staining with acetylated low density lipoprotein to visualize ECs on the graft luminal surface.

The grafts were then rinsed three times with HBSS, and the lumen treated with 0.025M $NH_4OH$ for 4.5 minutes to remove the ECs. The grafts were rinsed with HBSS, fixed with 0.25% glutaraldehyde for 24 hours at 23° C., followed by extensive washing in sterile normal saline.

The grafts were then incubated in Medium 199 overnight at 37° C., followed by incubation in ECGM for 4–6 hours to block and neutralize free and unreacted glutaraldehyde groups. The luminal space of each graft was filled with a suspension of ECs at a seeding density of $1.1 \times 10^6$ cell per ml. The grafts were wedged into culture tubes and incubated on a roller apparatus at 10 RPM at 37° C. for 7–14 days to establish the endothelial cell monolayer. Confirmation of EC coverage was carried out by scanning electron microscopy analysis and staining with acetylated low density lipoprotein to identify the presence of endothelial cells.

Example 4

(Derived Subendothelium Seeded with Endothelial Cells)

A commercially available 4 mm GORE-TEX® Vascular Graft was modified through the addition of subendothelium derived from a donor cow aortae. The vessel was obtained at slaughter and frozen at −20° C. until use. After opening with a longitudinal incision, the intimal surface was gently rubbed with a paper towel to ensure removal of endothelial cells remaining after the freezing-thawing cycle. Then, using a scalpel blade, the intimal surface of the donor vessel was carefully scraped, taking care to not penetrate the internal elastic lamina. The subendothelial matrix derived in this manner from approximately 5 cm of cow aorta was used for a single 4 mm×5 cm inventive graft. The scrapings from the cow aorta were suspended in about 50 ml HBSS and subjected to homogenization with a Verti-shear mixer for about 60 seconds. The homogenized subendothelium was allowed to sit for about 10 minutes to allow the larger clumps to settle out and the remainder of the homogenate decanted. The suspension was placed in a syringe and the inventive graft mounted on barbed fittings. The 4 mm GORE-TEX® Vascular Graft was wetted with 100% ethanol and the ethanol displaced with HBSS. An aliquot containing the scrapings was then forced through the pores of the graft, depositing the subendothelial extracellular matrix on the surface of the graft. The graft was sterilized in 70% ethanol overnight and rehydrated in a graded ethanol series into HBSS. The graft was then incubated in Medium 199 overnight followed by ECGM to equilibrate the graft to the culture medium. Endothelial cells were harvested and seeded onto the graft subendothelial surface by filling the graft lumen with a suspension of endothelial cells at a concentration of $1.1–1.3 \times 10^6$ cells/ml of ECGM. The graft was then capped at both ends, wedged into a culture tube, and placed into a 37° C. incubator on a roller apparatus for 7–10 days to allow the endothelial cells to establish a monolayer and become firmly attached. Endothelial cell coverage was confirmed by observing uptake of acetylated low density lipoprotein.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A blood contact material comprising:
    a synthetic base material comprising porous polytetrafluoroethylene;
    a substratum attached to the synthetic base material, said substratum comprising a preserved subendothelial matrix layer that supports attachment and growth of applied cardiovascular endothelial cells thereon;
    a layer of applied cardiovascular endothelial cells attached to the preserved subendothelial matrix layer;
    wherein the cardiovascular endothelial serve as a direct blood contact surface; and
    wherein, in the absence of cells attached to the substratum, the substratum servers as a direct blood contact surface.

2. The blood contact material of claim 1 wherein the synthetic base material comprises a tubular structure.

3. The blood contact material of claim 1 wherein the synthetic base material comprises at least a portion of a heart valve.

4. The blood contact material of claim 1 wherein the synthetic base material comprises a flexible sheet.

5. The blood contact material of claim 1 wherein the synthetic base material further comprises polymeric materials selected from the group consisting of polytetrafluoroethylene, polyethylene tetraphthalate, polypropylene, and fluorinated, ethylene propylene, either alone, or in combination.

6. The blood contact surface of claim 1, wherein
    the substratum contains at least one protein in a group consisting of chondroitin sulfate proteoglycans, fibronectin, collagen Type I, collagen Type III, collagen Type IV, and elastin.

7. The blood contact surface of claim 1 wherein the surface is formed through the following process:
    providing a donor blood vessel comprising an endothelial cell layer attached to a subendothelial matrix layer attached to a smooth muscle cell layer;
    stripping the endothelial cell layer from the subendothelial matrix layer of the donor blood vessel to produce a subendothelial matrix substratum substantially free of endothelial cells;
    preserving the subendothelial matrix; and
    applying cardiovascular endothelial cells to the substratum.

8. The process of claim 7 which further comprises:
    stripping the endothelial cell layer from the subendothelial layer by treating with a stripping solution.

9. The process of claim 8 wherein the stripping solution is an aqueous solution of ammonium hydroxide at a concentration ranging from about 0.01M to about 0.5M.

10. The process of claim 7 that further comprises:
    stripping the endothelial cell layer by freeze-thaw treating the endothelial layer.

11. The process of claim 7 which further comprises:
    stripping the endothelial cell layer by air dry treating the endothelial layer.

12. The process of claim 7, which further comprises:
    removing the subendothelial matrix layer from the donor blood vessel and applying the subendothelial matrix layer to a synthetic component, the subendothelial matrix layer serving as a direct blood contact surface.

13. The process of claim 7 which further comprises:
    treating the subendothelial matrix layer and any associated vascular tissue to reduce calcification by saturating the subendothelial matrix layer and any associated vascular tissue with a solution that predominantly extracts lipid components.

14. The process of claim 13 wherein the solution used to reduce calcification is a solution of chloroform and methanol.

15. The process of claim 13 which further comprises:
treating the subendothelial matrix layer with a fixative solution to preserve the subendothelial matrix layer.

16. The process of claim 15 wherein the fixative solution is a solution of ethanol.

17. The process of claim 15 wherein the fixative solution is a solution of glutaraldehyde.

18. A method of producing a blood contact surface which comprises:
providing a donor blood vessel comprising a layer of endothelial cells attached to a subendothelial matrix layer attached to a layer of smooth muscle cells;
treating the blood vessel so as to remove the endothelial cells while leaving the subendothelial matrix layer in situ to form a substratum;
employing the substratum as a direct blood contact surface in an appliance, in the absence of cells attached to the substratum;
growing vascular endothelial cells on the substratum to form a vascular endothelial cell layer; and
employing the vascular endothelial cell layer as a direct blood contact surface in an appliance.

19. The method of claim 18 which further comprises:
employing the substratum as an appliance comprising an artificial vascular prosthesis obtained from a donor blood vessel.

20. The method of claim 19 which further comprises:
surrounding the artificial vascular prosthesis along its length with a sheath comprising a material which permits the passage of macromolecules through the sheath, while resisting ingrowth of cells from tissue surrounding the artificial vascular prosthesis when implanted.

21. The method of claim 18, which further comprises:
extracting the subendothelial matrix layer from a donor blood vessel and applying the subendothelial matrix layer to a synthetic component, the subendothelial matrix layer serving as a direct blood contact surface.

22. The method of claim 21, which further comprises:
preserving the subendothelial matrix layer.

23. The method of claim 18 which further comprises:
treating the subendothelial matrix layer and any associated vascular tissue layers to reduce calcification with a solution that predominantly extracts lipid components.

24. The method of claim 23 wherein the solution used to reduce calcification is a solution of chloroform and methanol.

25. The method of claim 22 which further comprises:
treating the subendothelial matrix layer with a fixative solution to preserve the subendothelial matrix layer.

26. The method of claim 25 wherein the fixative solution is a solution of ethanol.

27. The method of claim 25 wherein the fixative solution is a solution of glutaraldehyde.

28. A method of producing a blood contact surface which comprises:
co-culturing endothelial cells and smooth muscle cells in vitro to establish an endothelial cell layer overlying a smooth muscle cell layer;
incubating the co-culture until a subendothelial matrix layer is formed between the donor endothelial cell layer and a smooth muscle cell layer by the interaction of the smooth muscle cells and the donor endothelial cells;
treating the co-cultured endothelial cell layer and the smooth muscle cell layer so as to remove the donor endothelial cells thereby forming a subendothelial matrix substratum;
employing the substratum as a direct blood contact surface in an appliance, in the absence of cells attached to the substratum;
growing vascular endothelial cells on the substratum to form an endothelial cell layer; and
employing the vascular endothelial cell layer as a direct blood contact surface in an appliance.

29. The method of claim 28 which further comprises:
removing the subendothelial matrix layer from the smooth muscle cell layer and applying the subendothelial matrix substratum to a surface of an artificial vascular prosthesis upon which the blood contact surface is to be located.

30. The method of claim 28 which further comprises:
co-culturing the endothelial cells and the smooth muscle cells in vitro on a surface of an artificial vascular prosthesis upon which the blood contact surface is to be located, in order to establish the endothelial cell layer overlying the smooth muscle cell layer.

31. The blood contact surface of claim 30 wherein
the artificial vascular prosthesis is a tubular vascular prosthesis having an interior surface and an exterior surface wherein the in vitro co-culture is conducted on the interior surface of the tubular vascular prosthesis.

32. The method of claim 28 that further comprises:
employing endothelial cells that are vascular endothelial cells.

33. The method of claim 28 which further comprises:
employing smooth muscle cells that are vascular smooth muscle cells.

34. The method of claim 28 which further comprises:
treating the subendothelial matrix layer with a fixative solution to preserve the subendothelial matrix layer.

35. The method of claim 34 wherein the fixative solution is a solution of ethanol.

36. The method of claim 34 wherein the fixative solution is a solution of glutaraldehyde.

37. An artificial vascular prosthesis which comprises:
a de-endothelialized subendothelial matrix layer preserved with a fixative, the substratum serving as foundation upon which vascular endothelial cells attach and grow to form a vascular endothelial cell layer;
wherein the vascular endothelial cell layer serves as a direct blood contact surface; and
wherein, in the absence of cells attached to the preserved subendothelial matrix layer, the preserved subendothelial matrix layer serves as a direct blood contact surface.

38. The artificial vascular prosthesis of claim 37 wherein, the subendothelial matrix layer is obtained from a donor blood vessel and preserved in situ in the donor blood vessel.

39. The artificial vascular prosthesis of claim 37 wherein, the subendothelial matrix layer is produced by in vitro co-culture of endothelial cells and smooth muscle cells and applied to a surface of an artificial vascular prosthesis which will serve as a direct blood contact surface.

40. The artificial vascular prosthesis of claim 37 wherein, the subendothelial matrix layer is produced by in vitro co-culture of endothelial cells and smooth muscle cells conducted on a surface of an artificial vascular prosthesis which will serve as a direct blood contact surface.

41. The artificial vascular prosthesis of claim 37, wherein, prior to preservation of the de-endothelialized subendothelial matrix layer, the de-endothelialized subendothelial matrix layer and any vascular tissue layers externally attached to the de-endothelialized subendothelial matrix layer are treated to reduce calcification.

* * * * *